US010086086B2

(12) United States Patent
Bosnyak et al.

(10) Patent No.: US 10,086,086 B2
(45) Date of Patent: Oct. 2, 2018

(54) PAYLOAD MOLECULE DELIVERY USING MOLECULAR REBAR

(71) Applicant: Molecular Rebar Design, LLC, Austin, TX (US)

(72) Inventors: Clive P. Bosnyak, Dripping Springs, TX (US); Kurt W. Swogger, Austin, TX (US); Nancy Henderson, Austin, TX (US); Paul Everill, Austin, TX (US)

(73) Assignee: Molecular Rebar Design, LLC, Austin, TX (US)

( * ) Notice: Subject to any disclaimer, the term of this patent is extended or adjusted under 35 U.S.C. 154(b) by 684 days.

(21) Appl. No.: 14/628,248

(22) Filed: Feb. 21, 2015

(65) Prior Publication Data

US 2015/0238476 A1   Aug. 27, 2015

Related U.S. Application Data

(60) Provisional application No. 61/943,297, filed on Feb. 21, 2014.

(51) Int. Cl.
| | | |
|---|---|---|
| *A61K 31/455* | (2006.01) | |
| *A61K 47/48* | (2006.01) | |
| *A61K 9/70* | (2006.01) | |
| *A61K 31/337* | (2006.01) | |
| *A61K 41/00* | (2006.01) | |
| *A61K 45/06* | (2006.01) | |
| *A61K 47/69* | (2017.01) | |

(52) U.S. Cl.
CPC ........ *A61K 47/48776* (2013.01); *A61K 9/703* (2013.01); *A61K 31/337* (2013.01); *A61K 31/455* (2013.01); *A61K 41/00* (2013.01); *A61K 45/06* (2013.01); *A61K 47/6901* (2017.08); *A61K 47/6925* (2017.08); *A61K 47/6949* (2017.08)

(58) Field of Classification Search
None
See application file for complete search history.

(56) References Cited

U.S. PATENT DOCUMENTS 7,708,979 B2 * 5/2010 Lowman ................ A61F 2/441
424/422

OTHER PUBLICATIONS

Mashat et al (Zippered release from polymer-gated carbon nanotubes. J. Mater. Chem.,22, 11503-11508 (2012)).*
Shen et al (Polyethyleneimine-Mediated Functionalization of Multiwalled Carbon Nanotubes: Synthesis, Characterization, and In Vitro Toxicity Assay. J. Phys. Chem. C, 2009, 113 (8), pp. 3150-3156).*
Rosca et al (Oxidation of multiwalled carbon nanotubes by nitric acid. Carbon. vol. 43, Issue 15, Dec. 2005, pp. 3124-3131).*
Ahmed et al., "Adsorption-Desorption Behavior of Polyvinyl Alcohol on Polystyrene Latex Particles", ACS Symp. Series 240 (1983). pp. 77-94.
Danielson, J, "NMR Studies of the amylois b-peptide", Ph.D. Thesis, Stockholm University (2007).
Yoong et al., "Enhanced cytotoxicity to cancer cells by mitochondria-targeting MWCNTs containing platinum (IV) prodrug of cisplatin", 35(2) Biomaterials (2013), pp. 748-759.
Luo et al., "Carbon nanotube nanoreservoir for controlled release of anti-inflammatory dexamethasone" 32(26) Biomaterials (Elsevier Sci. Pub.) (2011), pp. 6316-6323.
Wu et al., "PEGylated Multi-Walled Carbon Nanotubes for Encapsulation and Sustained Release of Oxaliplatin", 30(2) Pharmaceutical Res. (2012), pp. 412-423.
Wu et al., "Trojan-Horse Nanotube On-Command Intracellular Drug Delivery", 12(11) Nano Letters (2012), pp. 5475-5480.
Raoof et al., "Remotely triggered cisplatin release from carbon nanocapsules by radiofrequency fields", 34(7) Biomaterials (2013), pp. 1862-1869.

* cited by examiner

*Primary Examiner* — Jake M Vu
(74) *Attorney, Agent, or Firm* — Stephen P. Krupp

(57) ABSTRACT

In various embodiments a payload molecule or drug molecule delivery system is disclosed. The system comprises a plurality of functionalized discrete carbon nanotubes having specific properties. The composition can comprise a plurality of discrete carbon nanotubes that have at least a portion of the carbon nanotubes with a number average (ratio of number average contour length to end to end length) of greater than 1.1 and up to about 3. These discrete carbon nanotubes having the specified ratio of number average (tube contour length ($T_{CL}$) to number average tube end-end length ($T_{EE}$)) ratio are not only discrete (separated) from one another, but are also controlled in their alignment such that processability and mechanical strength properties are both enhanced. Utility of the molecular rebar composition includes, but is not limited to improved payload molecule delivery, such as drug delivery, into body of an animal, such as human.

28 Claims, 2 Drawing Sheets

— end to end length

— ·· contour length

PAYLOAD MOLECULE DELIVERY USING MOLECULAR REBAR

RELATED APPLICATIONS

This application is related to and claims priority from Provisional Patent Application No. 61/943,297 filed Feb. 21, 2014, the entire content of which is incorporated herein by reference.

BACKGROUND

Carbon nanotubes in various forms have been widely written about and disclosed. They have been reported to and provide significant improvements in mechanical strength and electrical properties to materials when properly dispersed in a discrete manner and well adhered or bonded to the matrix. Carbon nanotubes have surface areas in the range of about 100 $m^2$/gram for multiwall carbon nanotubes to about 2000 $m^2$/gram for single wall carbon nanotubes. These large surface areas are conducive to attach or associate medicaments. Even more useful would be to use the interior of the carbon nanotubes as vesicles for molecules. However, these carbon nanotubes, as made, are in the form of clusters like a bird's nest, or fibrils that consist of many tubes that are "clumped" together, making them less than ideal or even useful to be able to reach their full performance potential. The carbon nanotubes as made have closed ends thereby restricting access to the interior cavities. Carbon nanotube aggregations are unable to form uniform, homogeneous dilute solutions for injection or treatment of the human body. Discrete carbon nanotubes solve these problems because the tubes are separate and distinct from each other and can be maintained in that form without re-agglomerating in aqueous media. For drug delivery applications, is also desirable for the carbon nanotubes to flow through the fine needle or injection device with relative ease.

For drug delivery in the human body carbon nanotube surfaces have to be modified to increase their hydrophilicity to be able to be dispersed in the aqueous medium.

Furthermore, the surface modification or functionalization is required to enable biocompatibility and low toxicity for their medical applications.

The functionalization procedure of CNTs can be divided into two main approaches, that is, chemical bond attachment (covalent or ionic) and noncovalent or associative attachment (physioadsorption or physioabsorption).

If the drug is to be contained within the discrete carbon nanotube it may also considered to be important to treat the inside surface of the tube and/or the ends of the discrete tube to control the rate of inclusion of the drug molecule as well as the release rate of the drug molecule from the interior cavity. Selection of discrete carbon nanotubes, carbon nanotube length, diameter, and degree and type of functionalization are important parameters to control the kinetics of drug delivery. In some cases it may also be desirable to have the functionalization to include targeting molecules to specific target locations such as tumors.

A particular challenge with nanotubes is to effectively incorporate a drug inside the tube with little or no amount of the same drug on the outside of the tube.

SUMMARY

We have now discovered that discrete carbon nanotubes having specific properties can be used in payload or drug molecule delivery, especially for use in a human body.

In one aspect the invention is a composition comprising: a plurality of functionalized discrete single-wall, double-wall, or multi-wall carbon nanotubes having an innermost wall and an outermost wall, the inner-most wall defining an interior cavity, and at least one type of payload molecule; wherein the functionalized discrete carbon nanotubes are open on at least one end; and wherein greater than 30 weight percent of the at least one type of payload molecule is within the interior cavity of the discrete single-wall, double-wall or multi-wall carbon nanotubes.

In one aspect the invention is a composition comprising: a plurality of functionalized discrete, open ended multi-wall carbon nanotubes; wherein the functionalized discrete carbon nanotubes are aqueous-dispersible, and at least one type of payload molecule, the majority (preferably >60%, more preferably >75%, especially >95%) of which are located inside the discrete open ended multi-wall carbon nanotubes and wherein minimal drug molecules (e.g., <20%, preferably <10%, more preferably <5%) are located outside the walls of the discrete open ended multi-wall carbon nanotubes.

The functionalizing groups can be selected from the group consisting of bio-compatible surfactants. Preferred bio-compatible surfactants include, but are not limited to, PLA (polylactic acid), PVOH (polyvinyl alcohol), PEO (polyethylene oxide), PGLA (polyglycolic acid), CMC (carboxymethyl cellulose), PVP polyvinylpyrrolidone, PAA polyacrylic acid, aminoacids, peptides, polysaccharides and proteins (e.g., albumin). The open ended multi-wall discrete carbon nanotubes preferably comprise at least one end having attached thereto a bio-compatible polymer, amino acid, protein or peptide.

The attachment may be via covalent bonding, ionic bonding, hydrogen bonding or pi-pi bonding in nature. The functionalized discrete carbon nanotubes can include at least one tissue-targeting moiety. Use of tissue-targeting moieties is well known in the art to provide directed delivery of a drug to a particular tissue in vivo, such as a tumor tissue. The compositions may also be directed to certain cellular receptors, such as through receptor ligands attached to the functionalized carbon nanotube. In some disease states, such as but not limited to cancer, certain cellular receptors are either overexpressed or in a high-activity binding state. Direction of the compositions herein to cellular receptors advantageously provides a means of targeting a particular tissue. The at least one tissue-targeting moiety is selected from a group including, but not limited to, aptamers, nucleic acids, antibodies, antibody fragments, polysaccharides, peptides, proteins, hormones, receptor ligands, synthetic derivatives thereof, and combinations thereof. Various cellular recognition sites exist for these moieties, allowing for directed tissue targeting of the compositions.

At least one type of payload molecule is preferably at least partially released from the open ended multi-wall discrete carbon nanotubes by a mechanism comprising electromagnetic radiation exposure (e.g., MRI (Magnetic Resonance Imaging)), local pH changes, electrolyte balance, or biological (e.g., enzymatic) digestion of the biopolymer coat.

The plurality of functionalized discrete open ended multi-wall carbon nanotubes preferably comprises tube lengths of varying lengths. The tube length distribution may be monomodal, bimodal or multimodal. For tube length distributions comprising at least 2 groups of lengths, preferred is wherein each group's tube length varies on average by at least about 10% from the other group's average tube length to control drug release rates. Different length distributions may contain different payload molecules or different targeting moieties.

The plurality of functionalized discrete open ended multiwall carbon nanotubes comprises an average aspect ratio of from about 25 to about 200, preferably 25-150 and most preferably 40-120.

The plurality of functionalized discrete open ended multiwall carbon nanotubes can comprise 0.01 to 99% by weight of the formulation, preferably 0.1 to 99%, more preferably 0.25 to 95% by weight of the formulation.

Based on the desired rate of payload delivery 10% by weight or less of the discrete carbon nanotubes MR of the formulation can comprise L/D of about 100 to 200 and about 30% or more of the discrete carbon nanotubes (known and referred to herein as Molecular Rebar ("MR") of the formulation can comprise L/D of 40 to 80. The L/D of the discrete carbon nanotubes can be a unimodal distribution, or a multimodal distribution (such as a bimodal distribution). The multimodal distributions can have evenly distributed ranges of aspect ratios (such as 50% of one L/D range and about 50% of another L/D range). The distributions can also be asymmetrical—meaning that a relatively small percent of discrete nanotubes can have a specific L/D while a greater amount can comprise another aspect ratio distribution.

The payload molecule can be selected from the group consisting of a drug molecule, a radiotracer molecule, a radiotherapy molecule, a diagnostic imaging molecule, a fluorescent tracer molecule, a protein, a nucleic acid, and combinations thereof.

Exemplary types of payload molecules that may be covalently or non-covalently associated with the discrete functionalized carbon nanotubes disclosed herein may include, but are not limited to, proton pump inhibitors, H2-receptor antagonists, cytoprotectants, prostaglandin analogues, beta blockers, calcium channel blockers, diuretics, cardiac glycosides, antiarrhythmics, antianginals, vasoconstrictors, vasodilators, ACE inhibitors, angiotensin receptor blockers, alpha blockers, anticoagulants, antiplatelet drugs, fibrinolytics, hypolipidemic agents, statins, hypnotics, antipsychotics, antidepressants, monoamine oxidase inhibitors, selective serotonin reuptake inhibitors, antiemetics, anticonvulsants, anxiolytic, barbiturates, stimulants, amphetamines, benzodiazepines, dopamine antagonists, antihistamines, cholinergics, anticholinergics, emetics, cannabinoids, 5-HT antagonists, NSAIDs, opioids, bronchodilator, antiallergics, mucolytics, corticosteroids, beta-receptor antagonists, anticholinergics, steroids, androgens, antiandrogens, growth hormones, thyroid hormones, anti-thyroid drugs, vasopressin analogues, antibiotics, antifungals, antituberculous drugs, antimalarials, antiviral drugs, antiprotozoal drugs, radioprotectants, chemotherapy drugs, cytostatic drugs, cytotoxic drugs such as paclitaxel, and biologics, including proteins, such as antibodies and antibody fragments, as well as nucleic acids, including expression vectors, siRNAs, vaccines and the like.

In another aspect of the invention, a payload or drug molecule delivery system composition comprising discrete carbon nanotubes is disclosed, wherein at least a portion of discrete nanotubes has a ratio of number average value of ((tube contour length ($T_{CL}$)):(tube end to end length ($T_{EE}$))) of from about 1.1 to about 3, preferably from about 1.1 to about 2.8, more preferably from about 1.1 to about 2.4, most preferably from about 1.1 to about 2 and especially from about 1.2 to about 2.

Another aspect of the inventions is a payload or drug delivery system composition comprising a plurality of discrete carbon nanotubes wherein at least a portion of discrete nanotubes has a number average tube contour length ($T_{CL}$) of at least 10% greater than, and up to about 300% of, a number average tube end to end length ($T_{EE}$), wherein the number average $T_{CL}$ and $T_{EE}$ are obtained from the same batch of discrete carbon nanotubes.

In another aspect, in a payload or drug delivery system composition comprising a plurality of discrete carbon nanotubes having an average actual aspect ratio, of at least about 5% (volume) of the discrete carbon nanotubes having an apparent aspect ratio from about 50% to about 99% of the average actual aspect ratio of the discrete carbon nanotubes. The apparent aspect ratio can be from a low of about 60% or 70%, to as high as about 80%, 90%, about 99% of the actual aspect ratio.

The composition can have at least about 10% (volume), preferably 20%, more preferably 50%, most preferably 75%, and especially 95%, of the discrete carbon nanotubes that have an apparent aspect ratio from about 50% to about 99% of the actual aspect ratio of the discrete carbon nanotubes.

Another aspect of the invention is in a payload or drug delivery system composition comprising a plurality of discrete carbon nanotubes having a number average contour length $T_{CL}$, the improvement comprising at least about 5% (volume) of the discrete carbon nanotubes have a number average end-to-end tube length $T_{EE}$ low value from about 50%, 60%, or 70% to a high value of about 80%, 90%, or 99% of the number average $T_{CL}$.

The composition can have at least about 10% volume), preferably 20%, more preferably 50%, most preferably 75%, and especially 95%, of the discrete carbon nanotubes have a number average $T_{EE}$ from about 50% to about 99% of the number average $T_{CL}$ of the discrete carbon nanotubes.

The at least a portion of discrete nanotubes can have a number average value of (the ratio of discrete $T_{CL}$ to $T_{EE}$) of about 1.1 to as high as about 3, is greater than 5% by number, preferably greater than 20% by number and most preferably greater than 50% by number of tubes.

Processes to make the discrete carbon nanotubes are also described herein. These additional (and optional) steps can be selected from adding the discrete carbon nanotubes to a material to react with the oxidized discrete carbon nanotubes, adding surfactants, and adding other molecules including drugs.

DETAILED DESCRIPTION

Figure 1:
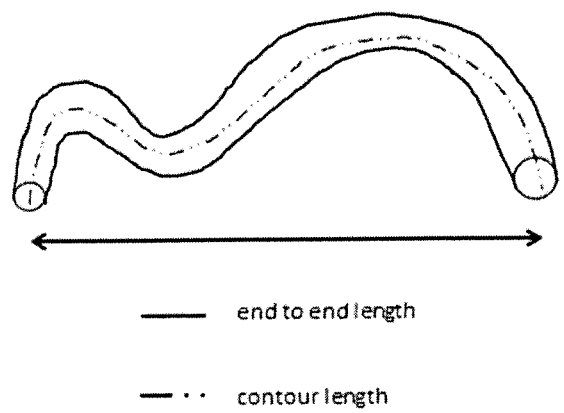
FIG. 1 shows a pictorial of a discrete carbon nanotube MR illustrating the contour length and end to end distance.
Figure 2:
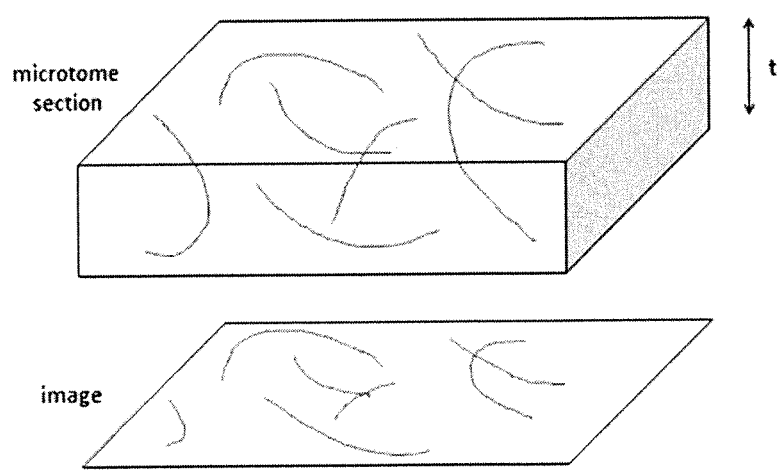
FIG. 2 shows a pictorial of a two dimensional view as would be seen in a transmission electron micrograph of a slice of a three dimensional representation of discrete carbon nanotubes MR of this invention.
Figure 3:
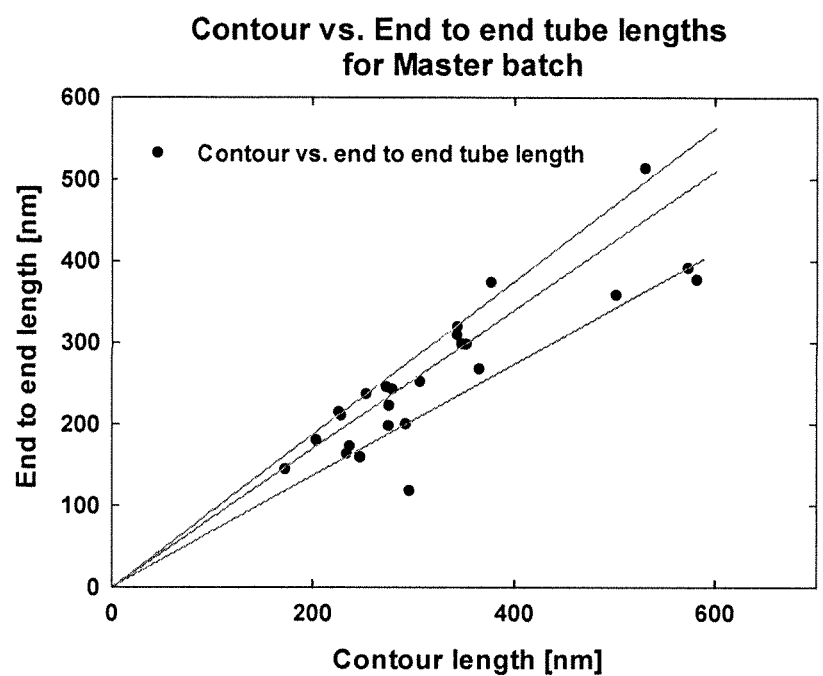
FIG. 3 shows a plot of end to end length vs contour length for discrete carbon nanotubes in a polymer matrix determined using scanning electron microscopy and a microtomed slice.

In the following description, certain details are set forth such as specific quantities, sizes, etc., so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009.

During the process of making discrete or exfoliated carbon nanotubes (which can be single, double and multi-wall configurations), the nanotubes are cut into segments with at least one open end and residual catalyst particles that are interior to the carbon nanotubes as received from the manufacturer are removed. This cutting of the tubes helps with exfoliation. The cutting of the tubes reduces the length of the tubes into carbon nanotube segments that are defined here as Molecular Rebar. Proper selection of the carbon nanotube feed stock related to catalyst particle type and distribution in the carbon nanotubes allows more control over the resulting individual tube lengths and overall tube length distribution. A preferred selection is where the internal catalyst sites are evenly spaced and where the catalyst is most efficient. The preferred aspect ratio (length to diameter ratio) is greater than about 25 and less than about 200 for a balance of viscosity and drug delivery kinetics performance. The selection can be evaluated using electron microscopy and determination of the discrete or exfoliated tube length distribution.

Molecular Rebar has oxidized species on the surface, also known herein as functionalized groups. In this disclosure, the amount of oxidation can be from about 1 to about 15% by weight of the dried carbon nanotubes. Oxidized species include but not limited to carboxylates, hydroxyls, lactones, and combinations thereof. The oxidized species can react advantageously with species such as, but not limited to, an acylchloride, epoxy, isocyanate, hydroxyl, or amine group. The Molecular Rebar may further comprise a biocompatible dispersing agent or surfactant, adhesively, ionically or covalently bonded to the Molecular Rebar surface. The biocompatible dispersing or surfactant molecule can be chosen such that the size of the surfactant molecule in the liquid media prevents it from entering within the discrete carbon nanotube. The selection of the minimum size of the surfactant molecule that cannot enter into a tube opening is related to the diameter of the tube opening and the hydrodynamic radius of the molecule in the liquid media.

Hydrodynamic radius, $R_H$, of polymer molecules in liquid media has been well-studied in the scientific literature, for example M. S. Ahmed, M. S. El-Aassar and J. W. Vanderhoff, ACS Symp. Series 240:77 (1983). Techniques to measure the radius of gyration commonly include viscometry and photon correlation spectroscopy. In the studies by Ahmed et al., the values of $R_H$ of polyvinyl alcohol adsorbed onto polystyrene particles of diameter 190 nm in water were found to follow an equation $R_H=0.03$ Mw$^{0.538}$.

The size of the surfactant molecule that can disperse the discrete carbon nanotube in aqueous media and is not expected to be able to enter within the cavity of the open ended carbon nanotube is preferably greater than about 30,000 Daltons, more preferably greater than about 60,000 Daltons and most preferably greater than about 100,000 Daltons. An example of a biocompatible polymer that is of size that does not fit within carbon nanotubes with an internal diameter opening of 5 nm is polyvinyl alcohol of molecular weight about 61,000 Daltons, available as Mowiol 10-98, supplied by Kuraray. It is also preferable that the biocompatible dispersing agent or surfactant, displaces the drug in part or wholly from the outermost surface of the nanotube.

TABLE 1

The Hydrodynamic Radius of Various Molecules in Water for Various Molecules

| Molecule | Molecular Weight, Daltons | Hydrodynamic Radius, nm |
|---|---|---|
| Niacin | 123 | 0.33 |
| Nicotine | 162 | 0.38 |
| Tryptophan | 204 | 0.43 |
| Scopolamine | 303 | 0.52 |
| Fentanyl | 332 | 0.54 |
| Desmopressin | 1069 | 0.88 |
| Insulin | 6000 | 2.1 |
| Cytochrome C | 11700 | 2.64 |
| Myoglobin | 15300 | 3.34 |
| Bovine serum albumin | 67000 | 7.0 |

The hydrodynamic radius, $R_H$ of single amino acids, small di- and tripeptides as well as denatured proteins fit an equation $R_H=0.027M^{0.5}$ nm. (J. Danielson. PhD. Thesis Stockholm University 2007). For PVOH this has been found to be $R_H=0.03M^{0.538}$ nm. It is recognized that the value of the hydrodynamic radius is also dependent on the solvent quality, i.e., $R_H$ will decrease for insulin in acid conditions versus neutral conditions. Likewise a change in temperature can also cause a change in values of $R_H$. This change in hydrodynamic radius may be conducive to fit molecules within the interior cavity of the discrete carbon nanotube; then to change the liquid media environment and force expansion of the molecules' hydrodynamic radius and cause expulsion of the drug molecule from the interior cavity, one needs to change the environment, such as for example, by changing liquid media environment temperature, pH or both.

Single-wall and double-wall carbon nanotubes typically have internal diameters of about 0.9 to about 1.2 nm.

Multi-wall carbon nanotubes typically have internal diameters from about 1.8 to about 50 nm. Molecules are considered unlikely to enter into open ended carbon nanotubes if their hydrodynamic radius is about 10% larger than that of the carbon nanotube opening. This means, for example looking at Table 1, that insulin, with a hydrodynamic radius of 2.1 nm would not be able to enter inside an opened single wall or double wall carbon nanotube. Likewise, bovine serum albumin with a hydrodynamic radius of 7 nm would not enter into an open ended multiwall carbon nanotube of internal diameter 5.5 nm. This means that the selection of the innermost wall diameter of the discrete carbon nanotube plays a key role in selecting the maximum size of molecule that can enter into the carbon nanotube.

The biocompatible dispersing or surfactant molecule can also be chosen to help solubilize a drug in an aqueous media such that the drug and surfactant conjugate can enter into an open ended nanotube, followed by the nanotube and contents being encapsulated with a larger biomolecule that cannot enter into the tube. The size of the surfactant molecule being able to enter into the nanotube is preferably less than about 10,000 Daltons, more preferably less than about 5,000 Daltons and most preferably less than about 2,000 Daltons. An example of this type of surfactant being able to enter into a multiwall nanotube is polyoxyethene sorbitan monostearate of molecular weight about 1309 Daltons and is commercially available as Tween-60 (Tween is a registered Trademark of Croda International PLC). As a result of the aforementioned, discrete carbon nanotubes, known and referred to herein as Molecular Rebar or MR, gives advantageous drug transport properties.

The internal tube diameter of the open ended carbon nanotube can be selected to allow a maximum size of the drug molecule to enter within the tube. This can be useful to select a certain size molecule from a mixture of molecules of different sizes. Open ended carbon nanotubes of different internal diameter tubes and/or different lengths can be used to control the rate of drug delivery, or combinations of drug types or sizes. Discrete open ended carbon nanotubes of differing functionality can also be used to control the rate of release of the drug to the treatment site.

The discrete oxidized carbon nanotubes (or DCNT), alternatively termed exfoliated carbon nanotubes, of the present disclosure can take advantage of properties such as electrical, thermal, physical and drug transport, offered by individual carbon nanotubes that are not apparent when the carbon nanotubes are aggregated into bundles. An example of properties offered by individual carbon nanotubes rather than bundled or associated carbon nanotubes would be to deliver drug concentrations more accurately and for individual carbon nanotubes to be preferentially oriented alongside cell walls or to enter within cells.

Discrete oxidized carbon nanotubes, alternatively termed exfoliated carbon nanotubes, are obtained from as-made bundled carbon nanotubes by methods disclosed in U.S. Ser. Nos. 13/164,456 and 13/140,029, the disclosures of which are incorporated herein by reference, are particularly useful in producing the discrete carbon nanotubes used in this invention. The bundled carbon nanotubes can be made from any known means such as, for example, chemical vapor deposition, laser ablation, and high pressure carbon monoxide synthesis. The bundled carbon nanotubes can be present in a variety of forms including, for example, soot, powder, fibers, and bucky paper. Furthermore, the bundled carbon nanotubes may be of any length, diameter, or chirality. Carbon nanotubes may be metallic, semi-metallic, semi-conducting, or non-metallic based on their chirality and number of walls. The discrete oxidized carbon nanotubes may include, for example, single-wall, double-wall carbon nanotubes, or multi-wall carbon nanotubes and combinations thereof. One of ordinary skill in the art will recognize that some of the specific aspects of this invention illustrated utilizing a particular type of carbon nanotube may be practiced equivalently within the spirit and scope of the disclosure utilizing other types of carbon nanotubes. However, for control of the desired structures of a plurality of discrete carbon nanotubes requires a specific control of chemistry, thermal and mechanical energy which varies according to the starting structure of the carbon nanotubes.

In particular for forming carbon nanotubes of this invention is the incorporation of a portion of structures called Stone-Wales defects which are the rearrangement of the six-membered rings of graphene into heptagon-pentagon pairs that fit within the hexagonal lattice of fused benzene rings constituting a wall of the carbon nanotubes. These Stone-Wales defects are useful to create sites of higher bond-strain energy for more facile oxidation of the graphene or carbon nanotube wall. These defects and other types of fused ring structures may also facilitate bending or curling along the length of the carbon nanotubes.

Stone-Wales defects are thought to be more prevalent at the end caps that allow higher degrees of curvature of the walls of carbon nanotubes. During oxidation the ends of the carbon nanotubes can be opened and also result in higher degrees of oxidation at the opened ends than along the walls. The higher degree of oxidation and hence higher polarity or hydrogen bonding at the ends of the tubes are thought useful to help increase the average contour length to end to end ratio where the tubes are present in less polar media such as oil. The ratio of the contour length to end to end distance can be advantageously controlled by the degree of thermodynamic interaction between the tubes and the medium. Surfactants and electrolytes can be usefully employed also to modify the thermodynamic interactions between the tubes and the medium of choice. Alternate means to influence the ratio of contour length to end to end ratio include the use of inorganic or ionic salts and organic containing functional groups that can be attached to or contacted with the tube surfaces.

General Process to Make Discrete Carbon Nanotubes (DCNT) or Molecular Rebar (MR)

As manufactured carbon nanotubes in the form of fibrous bundles can be obtained from different sources to make discrete carbon nanotubes. However, for the examples used herein, carbon nanotubes obtained from CNano 9000 are used. CNano carbon nanotubes have about 4% wt. residual catalyst. The average external tube diameter is about 13 nm (a later table herein lists other tube diameters of about 12.5 nm) as determined by scanning electron microscopy (SEM). Carbon nanotube manufacturers can have higher % impurities and much broader and higher diameter carbon nanotube distributions depending on manufacturing technique. Other tube manufacturers include Arkema and Southwest NanoTechnologies Inc.

Discrete carbon nanotubes (Molecular Rebar or MR) can be made using a variety of process conditions, processes, and catalysts. Tube diameter and diameter distributions are determined by and characteristic of these conditions. Resulting tube length and length distributions from the MR process are related to catalyst efficiency during carbon nanotube manufacture and process conditions, amount of catalyst incorporation within the tube, and type and distribution of defects within the walls of the carbon nanotube, as well as chemical, thermal and mechanical processes used to make Molecular Rebar. Preferably, substantially all of the discrete carbon nanotubes tube ends are open ended after the MR conversion process.

Functionalized carbon nanotubes of the present disclosure generally refer to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof. The discrete carbon nanotubes of this invention can include mixtures of different functionalization either on the same tube, or as mixtures of tubes with different functionalities, or both. Multiwall carbon nanotubes are preferred for functionalization as this leaves the inner walls non-functionalized, except for their ends, thereby maintaining properties such as good strength, electrical and thermal conductivity.

The discrete carbon nanotubes of the invention can be used as carriers of drugs in certain medical applications such as delivery of specific drugs to parts of the body of organs needing specific target application. Since the carbon nanotubes are discrete, open-ended and have specific L/D and are hollow, the drug delivery (or chemical delivery) can be tailored for specific molecule sizes to allow either attachment or association of the drug to the innermost and/or outermost tube surface. Other medical applications for the discrete carbon nanotubes with drugs whereby other properties of the discrete carbon nanotubes can be utilized such as strength include use in attaching ligaments or tendons to joints, or for bone grafting to help bone growth or re-growth under the proper conditions.

A General Method

One method to aid in the exfoliation and production of discrete carbon nanotubes of this invention is to use nitric acid solution (greater than about 60 weight % concentration, preferably above 65% nitric acid concentration, in water). Mixed acid systems (e.g., nitric and sulfuric) can be used also.

The starting bundles of carbon nanotube, CNT's, are added at about 1.2% weight by volume into the nitric acid at 50 degrees centigrade in a tank. Nitric acid is loaded first through a nozzle and CNT's are loaded through a hopper such that minimal CNT's are released. The mixture is then heated to 80° C. and stirred at for two hours while being continuously fed through an operating sonicator cell until the dispersion is uniform as judged by optical microscopy at 45× magnification.

EXAMPLES

One illustrative process for making discrete carbon nanotubes follows: A 16 liter mixture of 1.2% CNT's (obtained from CNano 9000) in 65% nitric acid, is pumped at 1.5 l/min. thru a 1000 watt sonicator cell using a 34 mm sonitrode. The back pressure is 30 psi, the amplitude is set at 85% and the recorded watts are at 500-600. After all of the 16 liters are pumped through the cell, the CNT slurry is drained back into the Sonicator Tank and the process is repeated until the CNT's are exfoliated and the Molecular Rebar has reached the desired specification, for example, as determined by optical microscopy and/or UV absorption. The number of times the material is processed through the sonicator is dependent on the amount of overall energy required to achieve the desired Molecular Rebar structure. For CNT's manufactured by CNano 9000, this energy is about 24000 to 40,000 joules/gram of CNT. The required energy for CNT's supplied by other manufacturers, may be different. The required amount of energy will vary also by the degree of exfoliation required for a given application, the medium the CNT's are in, temperature and desired amount of oxidation. The length or length distribution of the tubes can be influenced, for example, and not limited by, choosing different types of starting carbon nanotubes, by time of exposure to the acid mixture, temperature of operation, amplitude of operation of the sonication unit, power of sonication and flow rate of liquid through the sonicator cell. Oxidation type (carboxylic acid, alcohol, ketones, and aldehydes) and their concentration distribution at the exposed carbon nanotube surfaces are affected by temperature, time, and sonication energy. The oxidation level may also be reduced or eliminated by heating the tubes in an inert atmosphere at 600 degrees centigrade. The type of oxidation species desired may vary depending on the formulation requirements of each type of drug application. For example, if a minimum amount of biocompatible surfactant is desired for full dispersion of the discrete carbon nanotubes in aqueous media, this requires higher concentrations of carboxylic acid and hydroxyl groups on the tube surface. Increased amounts of functional groups can be gained, for example, but not limited to, using additional oxidizing agents such as peroxides, or azide containing molecules that insert at carbon-hydrogen bonds.

Once done, the entangled CNT's have been converted into discrete open ended carbon nanotubes, MR.

Filtration

After successful formation of a plurality of discrete open ended carbon nanotubes the slurry mix (no longer a CNT slurry but now an MR slurry) is more viscous than the original slurry at the same concentration, indicative of much higher aspect ratio of the MR (aspect ratio is length/diameter and in the example of using carbon nanotubes grade Flotube 9000 MR is about 60. A spherical bundle of carbon nanotubes is considered as an entity to have an aspect ratio of one.). The slurry is transferred to a filter to remove nitric acid and washed with clean water to at least pH 4, preferably greater than pH 5. This results in a filter cake with about 5% solids content.

Addition of Payload Molecule (e.g., a Drug)

Aqueous solubility of drug substances is an important parameter in pre-formulation studies of a drug product. Several drugs are sparingly water-soluble (soluble less than or equal to about 5% by weight of the drug) and pose challenges for formulation and dose administration. Organic solvents or oils and additional surfactants to create dispersions can be used. If the payload molecule is easily dissolved or dispersed in an aqueous media, the filter cake need not be dried. If the payload molecule is not easily dissolved or dispersed in aqueous media, the filter cake is first dried at 80° C. in vacuo to constant weight. It may be desirable to select the amount of oxidized species on the surfaces of the discrete carbon nanotubes to facilitate entry of hydrophobic or hydrophilic molecules. Adsorption or bonding of hydrophobic molecules to the outermost and innermost walls is facilitated by having less oxidized species on those carbon nanotube walls and ends of the discrete carbon nanotubes, for example less than 4% weight of oxidized species on the surfaces of the discrete carbon nanotubes. Conversely, the adsorption or bonding of hydrophilic molecules is facilitated 10 to 40% by weight of oxidized species on the surfaces of the discrete carbon nanotubes. Drug molecules that can be considered Lewis bases are preferred to adsorb onto the discrete carbon nanotubes. A Lewis base is considered a chemical species that can donate a lone pair of electrons, such as from a nitrogen, or oxygen, containing atom. Examples of Lewis bases include anions, such as sulfate and phosphate, amines and related pyridines. The payload molecule in the liquid media at the desired concentration is added to the discrete carbon nanotubes and allowed several hours to equilibrate within the tube cavity. The rate of insertion of the liquid media and payload molecule into the open ended carbon nanotube can be facilitated by introducing the liquid molecule and payload molecule while the carbon nanotubes are under vacuum. The mixture is then filtered to form a cake, less than about 1 mm thickness, then the bulk of the payload solution not residing within the tubes are removed by high flow rate filtration. The rate of filtration is selected so that relatively little time is allowed for the payload molecules to diffuse from the tube cavity. The filter cake plus payload drug is then subjected to an additional treatment if desired to attach or associate a large molecule such as an addition of an aqueous solution of a biopolymer, an aminoacid, protein or peptide that cannot enter into the inside of the open ended carbon nanotube. Alternatively another drug can be attached or associated Measurements of Oxidation, Length and Length Distribution, and Degree of Discrete Carbon Nanotubes.

Scanning electron microscopy is used to determine length distributions. The degree of oxidation can be measured by several tests such as Ols spectroscopy, energy dispersive X-ray and thermo-gravimetric analysis. Thermogravimetry, TGA, is conveniently used to determine the % by weight of oxidized species on the carbon nanotubes by a small sample (10-20 mg) of the filter cake dried in vacuum at 100° C. for 4 hours and the thermogravimetric analysis performed at 10° C./min heating rate in nitrogen from 100° C. to 600° C. The amount of oxidized species on the carbon nanotube is taken as the weight loss between 200 and 600° C. Ultraviolet spectroscopy, UV and SEM are used to determine the concentration and plurality of discrete tubes, i.e., carbon nanotubes not in a cluster or bundle. For UV analyses, for example, water is added to the wet cake to give a 0.5% weight carbon nanotube suspension, then sodium dodecylbenzene sulfonate is added at a concentration of 1.5 times the mass of oxidized carbon nanotubes. The solution is sonicated for 30 minutes using a sonicator bath at room temperature then diluted to a concentration of 2.5×10−5 g carbon nanotubes/ml. The solution of discrete carbon nanotubes will give a UV absorption at 500 nm of at least 1.2 absorption units for at least 15 minutes.

TABLE 2

Lengths (nm)

| | Condition 1 | Condition 2 | Condition 3 |
|---|---|---|---|
| Mean | 424 | 487 | 721 |
| Standard Error | 25.3 | 34.9 | 50 |
| Median | 407 | 417.0 | 672 |
| Standard Deviation | 177 | 281 | 315 |
| Sample Variance | 31461 | 79108 | 99418 |
| Kurtosis | −0.83 | 1.5 | −0.02 |
| Skewness | 0.03 | 1.2 | 0.64 |
| Range | 650 | 1270.0 | 1364 |
| Minimum | 85 | 85.0 | 161 |
| Maximum | 735 | 1355 | 1525 |

Condition 1 is an example of a narrow distribution with low mean length.
Condition 2 is an example of broad distribution with low mean length.
Condition 3 is an example of high mean length and broad distribution.

To determine tube lengths, a sample of tubes is diluted in isopropyl alcohol and sonicated for 30 minutes. It is then deposited onto a silica wafer and images are taken at 15 kV and 20,000× magnification by SEM. Three images are taken at different locations. Utilizing the JEOL software (included with the SEM) a minimum of 2 lines are drawn across on each image and measure the length of tubes that intersect this line.

Skewness is a measure of the asymmetry of a probability distribution. A positive value means the tail on the right side of the distribution histogram is longer than the left side and vice versa. Positive skewness is preferred which indicates means more tubes of long lengths. A value of zero means a relatively even distribution on both sides of the mean value.

Kurtosis is the measure of the shape of the distribution curve and is generally relative to a normal distribution. Both skewness and kurtosis values are unitless.

The following table shows representative values of discrete carbon nanotubes diameters:

TABLE 3

Diameter (unrelated to condition above)

| Mean Diameter (nm*) | | 12.5 |
|---|---|---|
| Mean Diameter (nm | | 11.5 |
| Kurtosis | 3.6 | |
| Skewness | 1.8 | |
| Calculated Aspect Ratio (L/D) | 34 | 39 58 |

*nm = nanometer

The improvement in flow processibility of the compositions can be determined using a rheometer, for example, utilizing concentric cylinders with a well-defined geometry to measure a fluid's resistance to flow and determine its viscous behavior. While relative rotation of the outer cylinder causes the composition to flow, its resistance to deformation imposes a shear stress on the inner wall of the cup, measured in units of Pa.

Table 4 below summarizes the ratios of (number average tube contour length (CL)) to (number average end to end tube length (EE)) as a function of mixing conditions (time and temperature) for discrete carbon nanotubes in a matrix styrene-butadiene rubber matrix. Mixing is accomplished using a Haake batch mixer in 10-80 min-1 RPM range. The summation of the number average ratios of (CL to EE) over the sample number size measured is also reported. "MB" is the abbreviation for master batch. As the data demonstrates, the ratio of Σ(CL)/n:Σ(EE)/n (first column) ranges from 1.26 to 1.42 for these experiments, showing that the ratio can be controlled through judicious use of mixing conditions. This means that for the discrete tubes in column 1, first row having Σ(CL)/n:Σ(EE)/n of 1.26, the $T_{EE}$ length is an average of about 79.4% of the $T_{CL}$ length. Said another way, the tubes are bent, or doubled back on themselves, or curled, such that the end to end length is about 80% the length of the contour length (or length fully stretched). This means that the tubes can be processed in a melt or highly concentrated liquid environment more favorably and will have useful rheological properties—lower viscosity in the melt or concentrated liquid under shear conditions. However, on dilution the tubes can become straighter. The other column shows number average (of the ratio of ($T_{CL}$:$T_{EE}$)). Similar results are expected when using other polymeric matrices such as, but not limited to, polyethylene oxide, polyacrylic acid, polylactic acid, polyvinyl alcohol, and polyvinylpyrrolidone.

TABLE 4

| Sample | n/ $\frac{\Sigma(CL)}{\Sigma(EE)}$ n | $T_{EE}$ as % of $T_{CL}$ from previous column | $\Sigma \frac{(CL) EE}{n}$ | $T_{EE}$ as % of $T_{CL}$ from previous column |
|---|---|---|---|---|
| MB @ 0 min./RT | 1.2592 | 79.4% | 1.2972 | 77% |
| MB @ 265 min./140° C. | 1.4256 | 70.1% | 1.9006 | 52.6% |
| MB @ 146 min./150° C. | 1.3173 | 75.9% | 1.6211 | 61.7% |
| MB @ 97 min./160° C. | 1.3770 | 72.6% | 1.7385 | 57.5% |

Any of the aspects disclosed in this invention with discrete carbon nanotubes may also be modified within the spirit and scope of the disclosure to substitute other tubular nanostructures, including, for example, inorganic or mineral nanotubes. Inorganic or mineral nanotubes include, for example, silicon nanotubes, boron nitride nanotubes and carbon nanotubes having heteroatom substitution in the nanotube structure. The nanotubes may include or be associated with organic or inorganic elements such as, for example, carbon, silicon, boron and nitrogen. Association may be on the interior or exterior of the inorganic or mineral nanotubes via Van der Waals, ionic or covalent bonding to the nanotube surfaces.

Example 1

A calibration curve for the UV absorption of niacin (Pyridine-3-carboxylic acid) as a function of the concentration of niacin in water is determined using the peak absorption wavelength at 262 nm. An extinction coefficient of 4060 l/mole-cm is determined. A solution is prepared by mixing 0.0578 grams of a plurality of discrete functionalized carbon nanotubes with 0.0134 grams of niacin in 25 ml of water (0.231 grams niacin/gram of carbon nanotube). The discrete carbon nanotubes employed have an oxidation level of 2% by weight of the discrete carbon nanotubes as determined by TGA, an average diameter of about 13 nm and length about 900 nm as determined from scanning electron microscopy. The oxidized species are approximately in the weight ratio of about ⅓ carboxylic acid, ⅓ hydroxyl groups and ⅓ ketones and lactones. Assuming the concentration of oxidized species per surface area is a constant, then this equates to having about 15% by weight of oxidized species on the outermost and innermost walls of the discrete open ended carbon nanotubes. The discrete tubes are allowed to settle and an aliquot of the fluid above the tubes removed hourly. The UV-vis absorption of this aliquot is measured and the resulting amount of niacin in the solution recorded. The amount of niacin in solution in the presence of the discrete functionalized carbon nanotubes stabilizes after 3 hours. The difference between the amounts of niacin remaining in the solution and the original amount is determined to be the amount of niacin associated with the discrete functionalized carbon nanotubes. The amount of niacin adsorbed by the carbon nanotubes after 5 hours is 0.08 g/g of discrete carbon nanotubes. Taking an average carbon nanotube length of 900 nm, external diameter of 13 nm and internal diameter of 5.5 nm, the available volume within the tubes is calculated as 0.097 $cm^3$ per gram of carbon nanotubes. Although not bound by theory, if the adsorption of niacin is the same concentration on the external wall as the innermost wall of the discrete carbon nanotube, the ratio of niacin adsorbed internally is about 2.4 times less than that adsorbed externally, i.e., internally about 0.025 g niacin/g discrete carbon nanotubes and externally about 0.055 g niacin/g discrete carbon nanotubes.

Example 2

Example 1 is repeated except with a plurality of discrete carbon nanotubes of similar length and diameter, but with 0.05% weight oxidized species. This equates to having about 4% by weight of oxidized species on the outermost and innermost walls of the discrete carbon nanotubes. The rate of absorption of niacin onto the discrete carbon nanotube surfaces in example 2 is approximately 17% more rapid than Example 1 and amount of niacin adsorbed after 5 hours is 0.088 g niacin/g discrete carbon nanotubes. Comparing Example 1 with Example 2 illustrates that the degree of oxidation on the carbon nanotube surfaces effects the adsorption of the drug. In this case a lower degree of oxidation on the discrete carbon nanotubes of Example 2 enhances the degree of adsorption of the niacin drug molecule.

Example 3

Discrete Carbon Nanotubes, PVOH and Niacin Added Together at the Same Time

A poly (vinyl alcohol), PVOH, of molecular weight 30-70 kDa and 87-90% hydrolyzed, obtained from Sigma Aldrich, is sufficiently large that it will not be adsorbed internally by the multiwall carbon nanotubes employed of average innermost tube diameter of about 5.5 nm. PVOH is added to a mixture of 0.0535 g of discrete carbon nanotubes, the same type as used for Example 1, and 0.0139 g niacin (i.e., 0.26 grams niacin to 1 gram carbon nanotubes) in 25 ml water. This is allowed to rest overnight. Using the same analytical procedure as Example 1, the total amount of niacin adsorbed to the discrete carbon nanotubes is determined to be 0.0561 grams niacin per gram of discrete carbon nanotubes. This value is about a 30% less than the 0.08 g niacin/g discrete carbon nanotubes in Example 1 and comparable to that estimated to be adsorbed by the external walls of the discrete carbon nanotubes, i.e., 0.055 g niacin/g discrete carbon nanotubes in Example 1. Example 2 illustrates that the polyvinyl alcohol restricts niacin from adsorbing on the external surface of the carbon nanotube and that PVOH is on the external surface of the discrete carbon nanotubes.

Example 4

Discrete Carbon Nanotubes Treated with Niacin then PVOH

Using the same discrete carbon nanotubes as Example 1, PVOH from Example 3 and the same analytical procedures, but PVOH is added after niacin had reached an equilibrium value of the adsorption. PVOH is added at a weight ratio of 0.23 PVOH:1 discrete carbon nanotubes. 25% wt. of the adsorbed niacin prior to addition of PVOH was released by subsequent addition of the PVOH. Example 4, taken with Example 3 further illustrates that PVOH is displacing niacin from the outermost walls of the discrete carbon nanotubes.

Example 5

Discrete Carbon Nanotubes Pretreated with PVOH then Niacin Added

Using the same discrete carbon nanotubes and PVOH as Example 3, and the same analytical procedures. 0.1028 g of discrete carbon nanotubes and 0.507 g of PVOH are added to 40 ml of water, shaken and left for about 20 hours. 0.019 g of niacin is then added and the mixture re-shook. The rate of increase of adsorbed niacin is rapid to 100 minutes and reaches a concentration of 0.0208 g niacin/g of discrete carbon nanotubes, thereafter the rate of adsorption is very slow, rising to 0.0226 after a further 85 minutes. Example 5 compared to Example 3 illustrates that the outermost surfaces of the discrete carbon adsorb faster than the innermost surfaces when the entrance of the carbon nanotube is blocked by a large molecule that cannot enter into the innermost surface.

Example 6

The Effect of Increasing pH on the Release of Niacin from the Surfaces of Discrete Carbon Nanotubes Using the same procedures as Example 1, but with 0.1032 grams of discrete carbon nanotubes, 0.0205 g niacin and 40 ml of water, after equilibrium of niacin adsorption 2 ml of sodium hydroxide, 0.1 molar concentration is added and stirred with a magnetic stirrer while monitoring the pH with a calibrated pH probe and meter. The pH drop reaches steady state after about 180 minutes and the final adsorption of niacin is determined by UV spectroscopy to be 0.03 g niacin/g discrete carbon nanotubes. Example 6 illustrates that increasing the pH from about 4 to about 7.3 can trigger the release of a drug from the discrete carbon nanotube surfaces.

Example 7

The Effect of Increasing pH on the Release of Niacin from the Surfaces of Discrete Carbon Nanotubes Using the same procedures as Example 4, except with a ratio of PVOH to discrete carbon nanotubes of 0.3:1 by weight. The equilibrium niacin concentration is 0.0476 g niacin/g discrete carbon nanotubes. A calibrated pH probe is inserted into the mixture and 2 ml of sodium hydroxide of concentration 0.1 Molar is added and the mixture stirred by a magnetic stirrer while continuously monitoring the pH change. The pH reduces from an initial value of 9.5 to 9.24 over 40 minutes, 9.24 to 8.9 over an additional 55 minutes, then 8.9 to 8.13 over further 110 minutes. In the time period overall the amount of niacin adsorbed on the discrete carbon nanotubes reduces by about 42%. Example 7 illustrates that increasing the pH from about 4.2 to 8 can trigger the release of a drug from the discrete carbon nanotube surfaces when encapsulated with molecules of radius of gyration larger than the diameter of the innermost wall of the open ended discrete carbon nanotubes.

Example 8

Using diethyl-4-methoxybenzylphosphonate, D4MBP, as a model compound for combretastatins. D4MBP is obtained from Sigma Aldridge. The UV extinction coefficient of D4MBP in water is determined to be 1411.5 l/mole-cm. Using the same discrete carbon nanotubes and procedure as Example 3, but with 0.00488 g in 20 ml of water and 0.0589 g of discrete carbon nanotubes of Example 1, the equilibrium concentration of D4MBP adsorbed onto the surfaces of the discrete carbon nanotubes is reached after 5 hours at room temperature and determined to be 0.053 g D4MBP/g discrete carbon nanotubes.

Example 9

As Example 8, but the weight of D4MBP is 0.00992 g and the weight of discrete carbon nanotubes is 0.0566 g in 20 ml of water. The equilibrium concentration of adsorbed D4MBP on discrete carbon nanotubes is 0.084 g D4MBP/g discrete carbon nanotubes. Comparison of Example 9 with Example 8 shows that increasing the initial concentration of D4MBP by 2× increases the adsorption weight ratio of D4MBP to discrete carbon nanotubes by about 58%.

Example 10

As Example 9, but the weight of discrete carbon nanotubes is 0.0566 g. After equilibrium of the D4BMP adsorption 0.0143 g PVOH as used in Example 3, is added. After about 24 hours the concentration of adsorbed D4MBP is 0.033 g D4MBP/g discrete carbon nanotubes. Using the same calculation as made in Example 1, and that PVOH cannot enter into the discrete carbon nanotube it is estimated that about 80% of the D4MBP originally residing on the outermost wall is displaced by the PVOH.

The invention claimed is:

1. A composition comprising: a plurality of functionalized discrete multi-wall carbon nanotubes having an innermost wall and an outermost wall, the innermost wall defining an interior cavity, and at least one type of payload molecule; wherein the functionalized discrete carbon nanotubes are open on at least one end; and wherein greater than 30 weight percent of the at least one type of payload molecule is within the interior cavity of the discrete multi-wall carbon nanotubes.

2. The composition of claim 1, wherein the functionalizing groups are selected from the group consisting of bio-compatible surfactants.

3. The composition of claim 2, wherein the bio-compatible surfactants are selected from the group consisting of polylactic acids, polyvinyl alcohols, polyethylene oxides, polyglycolic acid, polyvinylpyrrolidone, polyacrylic acids, carboxy methyl cellulose, peptides, polysaccharides, proteins and combinations thereof.

4. The composition of claim 1, wherein the multi-wall discrete carbon nanotubes comprise at least one end having attached thereto a bio-compatible polymer, amino acid, protein, peptide or combination thereof.

5. The composition of claim 1, wherein the multi-wall discrete carbon nanotubes further comprise a nucleic acid or protein which directs to a specific site, structure, or cellular component within a living body.

6. The composition of claim 1, wherein at least one type of payload molecule is at least partially released from the open ended multi-wall discrete carbon nanotubes by a mechanism comprising electromagnetic radiation exposure.

7. The composition of claim 1, wherein at least one type of payload molecule is encapsulated inside the multi-wall discrete carbon nanotube by a surfactant or polymer on the surface of the carbon nanotube.

8. The composition of claim 6, wherein at least one type of payload molecule is at least partially released from the open ended multi-wall discrete carbon nanotube by removing the surfactant or polymer from the surface by a change in pH or ionic concentration.

9. The composition of claim 1, wherein the plurality of functionalized discrete open ended multi-wall carbon nanotubes comprises tube lengths of varying lengths.

10. The composition of claim 1, wherein the plurality of functionalized discrete open ended multi-wall carbon nanotubes comprises tube lengths comprising at least 2 groups of lengths, wherein each group's tube length varies on average by at least about 10% from the other group's average tube length.

11. The composition of claim 1, wherein the plurality of functionalized discrete open ended multi-wall carbon nanotubes comprises multimodal tube lengths.

12. The composition of claim 1, wherein the payload molecule is selected from the group consisting of a drug molecule, a radiotracer molecule, a radiotherapy molecule, diagnostic imaging molecule, fluorescent tracer molecule, a protein molecule, and combinations thereof.

13. In a payload molecule delivery system composition comprising carbon nanotubes and at least one payload molecule, the improvement comprising using functionalized discrete carbon nanotubes, wherein the functionalized discrete carbon nanotubes are aqueous-dispersible, having an innermost wall and an outermost wall, the inner-most wall defining an interior cavity; wherein the functionalized discrete carbon nanotubes have an apparent aspect ratio and an average actual aspect ratio and are open on at least one end; and wherein greater than 30 weight percent of the at least one type of payload molecule is within the interior cavity of the discrete multi-wall carbon nanotubes; wherein at least about 5% (volume) of the functionalized discrete carbon nanotubes have an apparent aspect ratio from about 50% to about 99% of the average actual aspect ratio of the discrete carbon nanotubes.

14. The composition of claim 7, comprising greater than 4 weight percent carbon nanotubes, wherein upon dilution by 50%, the effective aspect ratio of the carbon nanotubes number average value of the discrete tube contour length to end to end distance increases by at least 10%.

15. The composition of claim 1, wherein the plurality of functionalized discrete open ended multi-wall carbon nanotubes comprises multimodal internal diameters.

16. The composition of claim 1, wherein at least one type of payload molecule is encapsulated inside the multi-wall discrete carbon nanotube by a surfactant or polymer on the surface of the carbon nanotube wherein the hydrodynamic radius of the surfactant or polymer in aqueous media is larger than the internal diameter of the discrete open ended carbon nanotube.

17. The composition of claim 1, wherein the outermost and innermost surfaces of the discrete carbon nanotube have less than about 4% by weight of carboxylate and hydroxyl moieties and wherein the payload molecule is sparingly soluble in water.

18. The composition of claim 1, wherein the outermost and innermost surfaces of the discrete carbon nanotube have more than about 4% by weight and less than about 40% by weight of carboxylate and hydroxyl moieties; and wherein the payload molecule is soluble in water.

19. The composition of claim 1 wherein about 10% or less by weight of the functionalized discrete carbon nanotubes have an aspect ratio (L/D) of about 100-200 and about 30% or more of the functionalized discrete carbon nanotubes have an aspect ratio (L/D) of about 40-80.

20. The composition of claim 19 wherein about 10% by weight of the functionalized discrete carbon nanotubes have an aspect ratio (L/D) of about 100-200 and about 30% or more of the functionalized discrete carbon nanotubes have an aspect ratio (L/D) of about 40-80.

21. The composition of claim 11 wherein the multimodal distribution of tube lengths is asymmetric.

22. The composition of claim 20 wherein the plurality of functionalized discrete multi-wall carbon nanotubes comprises an asymmetric, multimodal distribution of tube lengths.

23. The composition of claim 1, wherein greater than 60 weight percent of the at least one type of payload molecule is within the interior cavity of the discrete multi-wall carbon nanotubes.

24. The composition of claim 1, wherein greater than 75 weight percent of the at least one type of payload molecule is within the interior cavity of the discrete multi-wall carbon nanotubes.

25. The composition of claim 1, wherein greater than 95 weight percent of the at least one type of payload molecule is within the interior cavity of the discrete multi-wall carbon nanotubes.

26. The composition of claim 1, wherein less than 20 weight percent of the at least one type of payload molecule is located outside the walls of the discrete multi-wall carbon nanotubes.

27. The composition of claim 1, wherein less than 10 weight percent of the at least one type of payload molecule is located outside the walls of the discrete multi-wall carbon nanotubes.

28. The composition of claim 1, wherein less than 5 weight percent of the at least one type of payload molecule is located outside the walls of the discrete multi-wall carbon nanotubes.

* * * * *